(12) United States Patent
Chung et al.

(10) Patent No.: US 7,488,431 B2
(45) Date of Patent: Feb. 10, 2009

(54) LIPIODOL-FERROFLUID, AND A PROCESS FOR PREPARATION THEREOF

(75) Inventors: Jen-Chieh Chung, Jiaan Village (TW); Min-Nan Chen, Taipei (TW); Ching-Tsuen Huang, Longtan Shiang (TW)

(73) Assignee: Institute of Nuclear Energy Research Atomic Energy Council, Taoyuan County (TW)

( * ) Notice: Subject to any disclaimer, the term of this patent is extended or adjusted under 35 U.S.C. 154(b) by 324 days.

(21) Appl. No.: 11/448,051

(22) Filed: Jun. 7, 2006

(65) Prior Publication Data
US 2007/0190179 A1   Aug. 16, 2007

(30) Foreign Application Priority Data
Feb. 16, 2006   (TW)   ............... 95105175 A

(51) Int. Cl.
*H01F 1/44* (2006.01)
*A61K 9/10* (2006.01)
*A61K 36/66* (2006.01)

(52) U.S. Cl. .................. 252/62.52; 424/1.65; 424/484; 977/904; 977/838; 977/787

(58) Field of Classification Search ............. 252/62.52; 424/1.65, 484; 977/904, 838, 787
See application file for complete search history.

(56) References Cited

U.S. PATENT DOCUMENTS

| | | | | |
|---|---|---|---|---|
| 4,604,222 | A | 8/1986 | Borduz et al. | 252/62.52 |
| 4,687,748 | A | 8/1987 | Schroeder | 436/526 |
| 5,124,060 | A | 6/1992 | Yokouchi et al. | 252/62.51 |
| 6,068,785 | A | 5/2000 | Raj et al. | 252/62.52 |
| 6,140,001 | A | 10/2000 | Miyaji et al. | 430/106.6 |
| 6,743,371 | B2 | 6/2004 | John et al. | 252/62.52 |

FOREIGN PATENT DOCUMENTS

| | | |
|---|---|---|
| TW | 319773 | 11/1997 |
| TW | 334438 | 6/1998 |

*Primary Examiner*—C. Melissa Koslow
(74) *Attorney, Agent, or Firm*—WPAT.P.C.; Justin King

(57) ABSTRACT

The present invention discloses a lipiodol-ferrofluid, and a process for preparation thereof, wherein the lipiodol-ferrofluid includes the ferrofluid including a magnetic component, $\gamma\text{-Fe}_2O_3$ or $Fe_3O_4$; and the lipiodol.

19 Claims, 2 Drawing Sheets

LIPIODOL-FERROFLUID, AND A PROCESS FOR PREPARATION THEREOF

FIELD OF THE INVENTION

The present invention relates lipiodol-ferrofluid, and a process for preparation thereof, wherein the lipiodol-ferrofluid includes the ferrofluid including a magnetic component, $\gamma\text{-Fe}_2\text{O}_3$ or $\text{Fe}_3\text{O}_4$; and the lipiodol. With the effect of external magnetic field, the lipiodol-ferrofluid can stay at a specific area in an organism, and then generated heat by high frequency waves, to achieve a high temperature treatment or diagnosis.

BACKGROUND OF THE INVENTION

Magnetic materials have been commonly and widely used in or applied to magnetic tapes and disks, recorders, magnetic switches, and seals, etc. Recent years, applying magnetic materials to new fields has been developing, the new fields including the medicine preparation, the purification of protein and DNA in biomedical field, and the management and treatment of environmental waste. For example, by using magnetic materials to result magnetically responsive spheres disclosed by U.S. Pat. No. 4,687,748, the application of magnetic materials in cell separation, affinity purification or immunochemical assays is possible. The separation of a mixture to have the desired component or product is, therefore able to be reached by using a properly magnetic material, together with its related technical skills.

The magnetic materials, as mentioned above, are magnetic liquids, also so-called "ferrofluids." In view of a target subject treated by such a magnetically separation technique, techniques with under external magnetic field, have been developed as follows: (1) when the sample having magnetic characteristic, separating the magnetically desired component from the sample, and (2) when the sample not having magnetic characteristic, prior to the process of separation, performing the combination of the sample with a magnetic material. The magnetic material in (2) will be a key in the combination process.

The process for preparing the magnetic material varies with different field and needs, and includes techniques of (1) mechanical grinding, for example, U.S. Pat. No. 4,604,222 disclosing the method of ball milling and grinding for preparing the ferrofluid composition by mixing ferromagnetic particles, a cationic surfactant, and organic liquid carriers such as glycol or ester, and then grinding the obtained mixture, the ferrofluid composition obtained being used to improve electrical conductivity in sealing computer disc drives and in sputtering apparatus in semiconductive industry; (2) oxidation, for example, U.S. Pat. No. 6,140,001 disclosing iron oxide magnetic particles prepared by oxidation of oxygen and ferrous (II) hydroxide, including by mixing a solution of a soluble phosphate compound, such as sodium orthophosphate, a solution of ferrous ion, with a solution of hydroxide of an alkali metal or of an alkaline earth metal; and (3) chemical co-precipitation, for example, U.S. Pat. No. 6,743,371 disclosing a magneto sensitive fluid composition exhibiting electrical switching as well as magnetorheological characteristics in the presence of external magnetic field, the composition prepared by mixing nickel-zinc ferrite or manganese-zinc ferrite and any conductive metallic or non metallic powder such as silver, graphite powder.

However, the disadvantages also exit in above processes, the timing for operation mechanical grinding taking around 2-6 weeks, chemical co-precipitation creating chemical waste, comprising un-reacted metal salt solutions and uncoated particles in aqueous and nonaqueous media needed to be disposed of in proper compliance with environmental regulations. The waste removal adds to the cost of manufacturing the ferrofluids.

Regarding the process for preparing magnetic materials, specifically, a ferrofluid, surface treatment of magnetic particles is necessary, so as to effectively avoid aggregation of particles due to attraction of magnetic characteristics thereof, and improve the dispersion in the liquid carrier. The way of surface treatment, for example, is different from water- or oil-based ferrofluids.

In terms of preparation of oil-based ferrofluids, U.S. Pat. No. 5,124,060 disclosing a magnetic fluid prepared by adding the low boiling organic solvent and the dispersant having oleophilic groups to fine ferromagnetic particles to obtain an intermediate medium, separating the fine particles of poor dispersibility from the intermediate medium and, then adding the less volatile organic solvent and heating the resulting material to evaporate the low boiling organic solvent. The magnetic fluid composition can be used for sealing devices in computer hard disk driver or vacuum apparatus. Another example disclosed by U.S. Pat. No. 6,068,785, the oil-based ferrofluid is prepared by grinding a slurry formed of particles of a non-magnetic oxide of iron $\alpha\text{-Fe}_2\text{O}_3$, an oil carrier liquid, such as Ampro Type II oil, and a surfactant, such as polyolefin anhydride. Again, their non-economical impact is the disadvantage.

Furthermore, the application of conventionally oil-based ferrofluid, as mentioned previously, is primarily limited to magnetic memory device, sealing devices in computer hard disk driver or vacuum apparatus, but not to organism. While, in addition to the disadvantages of the process for preparing ferrofluid, as mentioned previously, $\alpha\text{-Fe}_2\text{O}_3$ used in the process, as mentioned above, for preparing ferrofluid is not a magnetic conductive material and is hard to perform magnetic transfer. Likewise, the unsuitable for many applications of water-based ferrofluids is left the room to improve the preparation and application of ferrofluid.

Accordingly, there is a need for a ferrofluid suitable for being used in an organism, and a process thereof is economical and efficient.

SUMMARY OF THE INVENTION

Accordingly, the aspect of this invention provides a lipiodol-ferrofluid, applicable in an organism, the lipiodol-ferrofluid comprising: (a) ferrofluid, and (b) lipiodol; wherein the weight to volume ratio of the ferrofluid to the lipiodol ranges from 10 to 40% (g/ml).

The another aspect of this invention provides a process for preparing lipiodol-ferrofluid, no need in using the conventional mechanical grinding method, the process comprising steps of: (a) preparing ferrofluid; (b) adding lipiodol to the ferrofluid by the weight to volume ratio of the ferrofluid to the lipiodol ranging from 10 to 40% (g/ml); and (c) dispersing the ferrofluid in the lipiodol.

Although a particular embodiment of the invention has been described in detail for purposes of illustration, various modifications and enhancements may be made without departing from the spirit and scope of the invention. Accordingly, the invention is not to be limited except as by the appended claims.

DETAILED DESCRIPTION OF THE INVENTION

Figure 1:
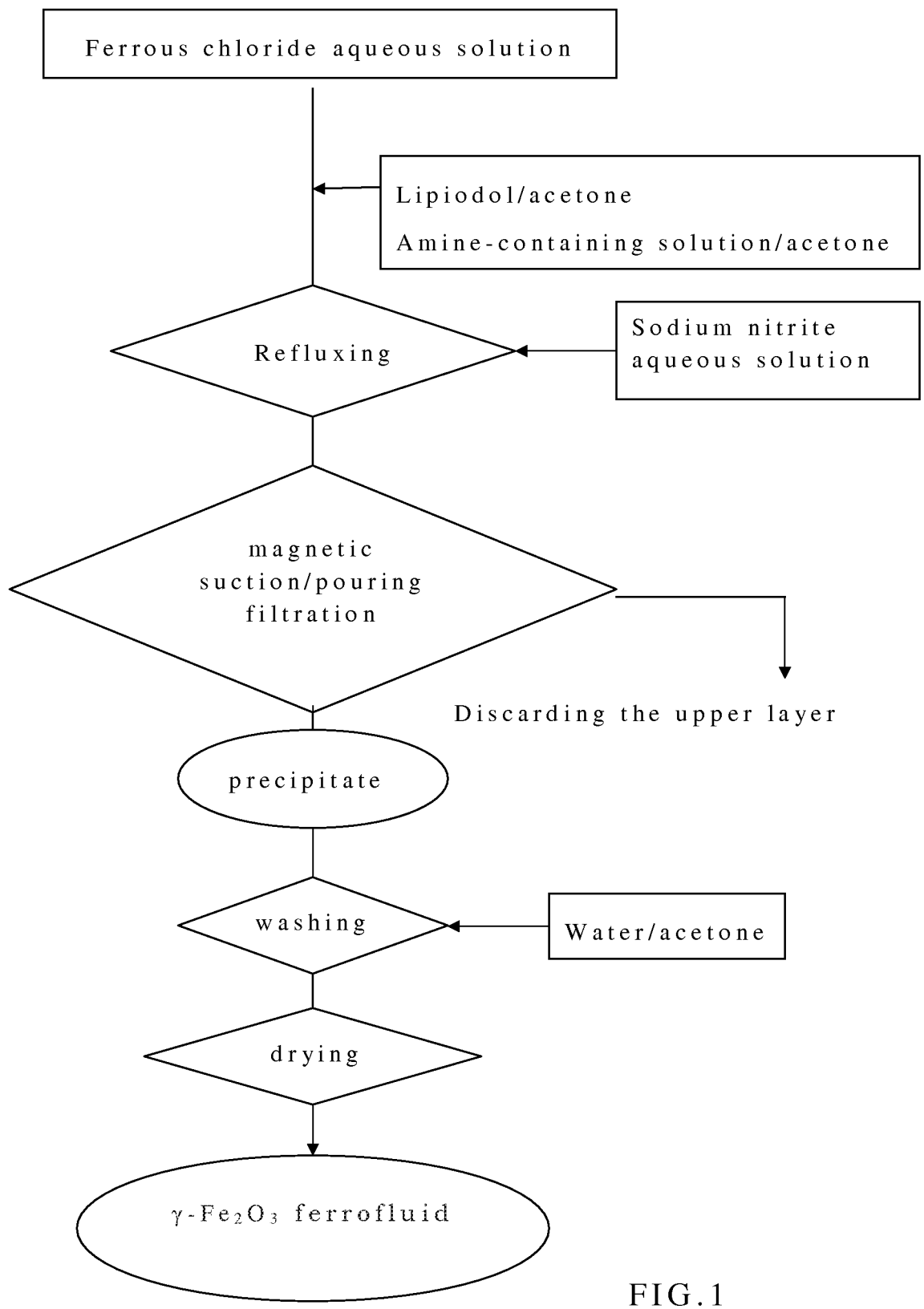
FIG. 1 is a process for preparing a ferrofluid including a $\gamma$-$Fe_2O_3$ material according to a preferred embodiment of the present invention.

The present invention mainly is to provide a lipiodol-ferrofluid, and a process for preparation thereof, wherein the lipiodol-ferrofluid includes the ferrofluid including a magnetic component, $\gamma$-$Fe_2O_3$ or $Fe_3O_4$; and the lipiodol. With the effect of external magnetic field, the lipiodol-ferrofluid can stay at a specific area in an organism, and then generated heat by high frequency waves, to achieve a high temperature treatment or diagnosis.

Lipiodol is an iodinated ethyl ester derived from poppy seed oil, and is widespread used as an X-ray contrast agent. With the latest findings of longer retention time or poor metabolic ability by lipiodol in the liver cells of organism, the process for preparing Y-90- and Re-188-Lipiodol were disclosed by TW334438 and TW319773 of this Assignee/Applicant herein taken as references in this application, wherein the isotope labeled lipiodol showed its efficiency in the treatment in radiation diagnosis.

The advantage of combination of ferrofluid with lipiodol being expected, as well as the process thereof, is capable of being shown by this invention. In order to make ferrofluid dispersed in lipiodol, the nano-grade ferrofluid firstly is prepared, having a particle size ranging from 20-150 nm, preferably 60-100 nm. Adding lipiodol to the ferrofluid, and mixing well to be lipiodol-ferrofluid, while not influencing the features of lipiodol, for example, the isotope labeled lipiodol. Further, with the guidance by the effect of external magnetic field, the lipiodol-ferrofluid can stay at a specific area, and then generated heat by high frequency waves, so as to achieve the elimination of the target cells with a high temperature, around ranging from 38 Celcius Degree to 50 Celcius Degree, preferably 42 Celcius Degree, which causes the effect of hyperthermia to the target cells. Therefore, a pharmaceutical composition comprising the lipiodol-ferrofluid as defined in claim 1 and a pharmaceutical acceptable carrier, could be manufactured.

One experimental process for preparing lipiodol-ferrofluid, specifically, comprising preparing oileophilic and nano-grade ferrofluid by adding ferrous chloride aqueous solution to the mixture of lipiodol and acetone, and then dripping slowly ethylenediamine aqueous solution while being heated to 60 Celcius Degree to 90 Celcius Degree, preferably 80 Celcius Degree for 3 hours, further dripping sodium nitrite aqueous solution and stirring constantly, the lipiodol-ferrofluid having a dark brown $\gamma$-$Fe_2O_3$ material then being obtained.

Another experimental process for preparing lipiodol-ferrofluid specifically, comprising preparing oileophilic and nano-grade ferrofluid by adding ferrous sulphate aqueous solution to the solution of a metal complexing agent, such as diethylenetriaminepentaacetic acid (DTPA), and then dripping slowly the alkaline aqueous solution while being heated at a proper temperature and a period of time, the lipiodol-ferrofluid having a $Fe_3O_4$ material can be obtained.

The feature of the process is capable to conduct the process at low or general working-temperature, but no need through sintering, and by surface treating the ferrous material to combine oileophilic functional groups of a solution needed in the process. Furthermore, the final product of this invention of lipiodol-ferrofluid is easily prepared by aseptic filling the lipiodol to the obtained ferrofluid according this invention, by the ratio around 10% to 40% (g/ml), preferably 30% (g/ml), which is conveniently to be used in clinical application.

More, lipiodol of lipiodol-ferrofluid of this invention, before being mixed with ferrofluid, could be labeled, as mentioned before, by isotopes, such as Y-90 and Re-188, so as to express the characteristics of tracing and radiation and magnetic property in an organism.

The above description, however, is only the preferable embodiment of the invention and cannot be used as a limitation for the scope of implementation of the invention. Any variation and modification made from the scopes claimed from the invention all should be included within the scope of the present invention, and hope your esteemed reviewing committee member examine this application favorably and permit it as a patent wishfully.

EXAMPLE 1

Preparation of Lipiodol-Ferrofluid ($\gamma$-$Fe_2O_3$)

FIG. 1 is a process for preparing a ferrofluid including a $\gamma$-Fe2O3 material according to a preferred embodiment of the present invention. Mixing and stirring 0.5~1.5 ml, preferably 1 ml lipiodol, with 15~25 ml, preferably 20 ml acetone, and the solution of 4~8 g, preferably 6 g ferrous chloride (containing 2~6 hydrate, preferably 4 hydrate) (Merck, Germany) in 5~15 ml, preferably 10 ml water; during stirring, adding the mixture of 5~15 ml, preferably 10 ml of an amine-containing solution, such as ethylenediamine solution, and 30~50 ml, preferably 40 ml acetone; refluxing at 60 to 90 Celcius Degree, preferably 80 Celcius Degree. Then, dripping slowly the solution of 5~15 mg, preferably 10 mg sodium nitrite in 10~30 ml, preferably 20 ml water, and refluxing at 80 Celcius Degree at least one hour. Obtaining the precipitate by a proper way, such as magnetic suction/pouring filtration; washing the precipitate in order by 2~20 ml, preferably 10 ml of acetone, and reagent-grade water more than twice, then drying the washed precipitate. Aseptic filling the lipiodol solution (Guerbet, France) to the ferrofluid, by the ratio of ferrofluid to lipiodol, around 10% to 40% (g/ml), preferably 30% (g/ml), to form pre-lipiodol ofluid. Finally, dispersing or vibrating the pre-lipiodol ferrofluid by ultrasound.

Lipiodol-ferrofluid including a $\gamma$-$Fe_2O_3$ material according to a preferred embodiment of the present invention therefore is obtained. The particle size of the magnetic component, the $\gamma$-$Fe_2O_3$ material ranges from 20 to 150 nm, preferably 60 to 100 nm.

Ethylenediamine, mentioned above, could be replaced by hexamethylenetetramine.

EXAMPLE 2

Preparation of Lipiodol-Ferrofluid ($Fe_3O_4$)

Figure 2:
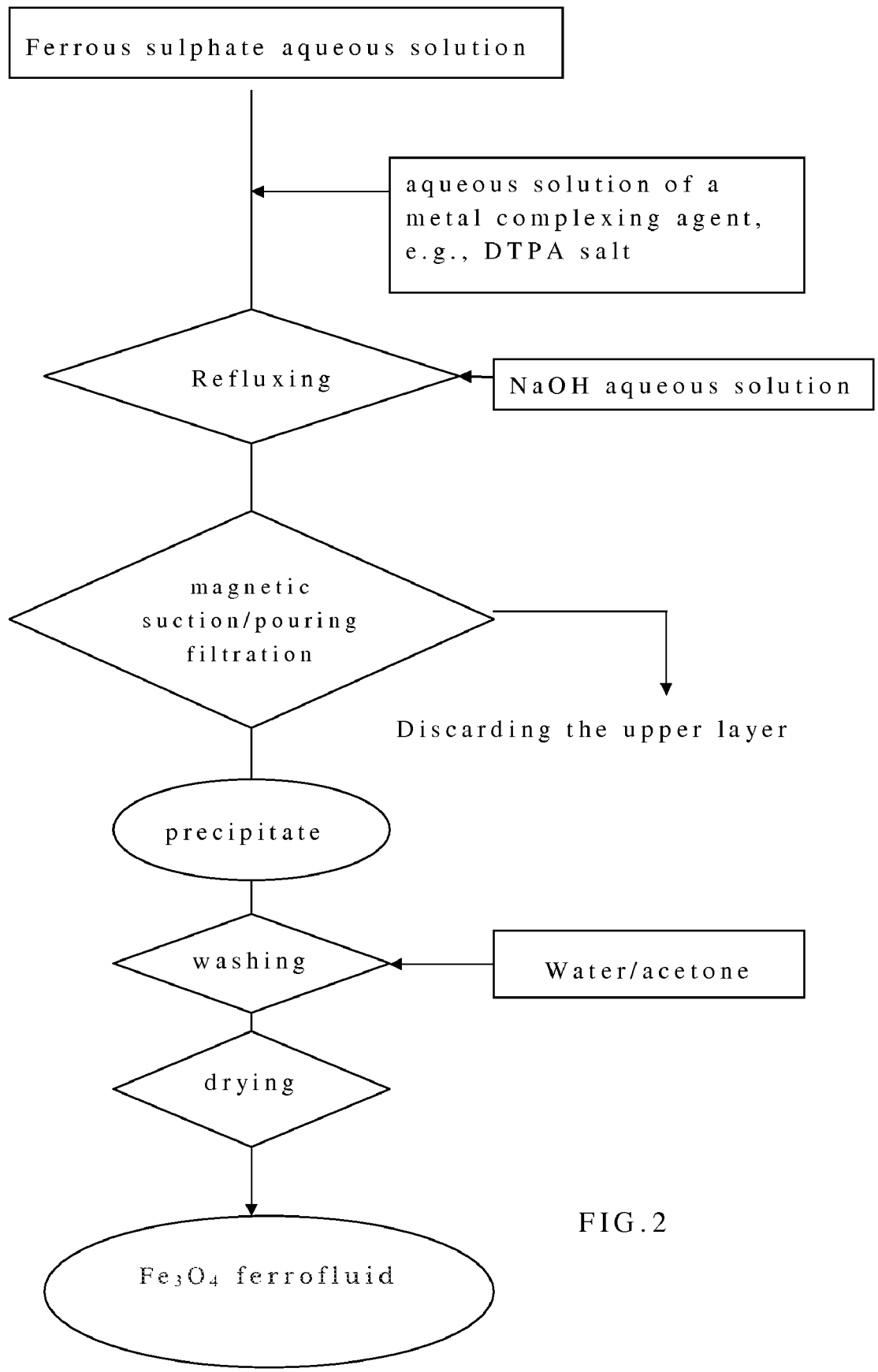
FIG. 2 is a process for preparing a ferrofluid including a $Fe_3O_4$ material according to a preferred embodiment of the present invention.

FIG. 2 is a process for preparing a ferrofluid including a $Fe_3O_4$ material according to a preferred embodiment of the present invention. Mixing and stirring the solution of 5~9 g, preferably 7.8 g a metal complexing agent, such as the salt of diethylenetriaminepentaacetic acid (DTPA) in 5~15 ml, preferably 10 ml water, with the solution of 3~7 g, preferably 5.5 g ferrous sulphate (containing 5~9hydrate, preferably 7 hydrate) (Merck, Germany) in 30~50 ml, preferably 40 ml water; refluxing at 80 to 120 Celcius Degree, preferably 110 Celcius Degree. During stirring, further dripping slowly the solution of 1~5 g, preferably 3 g alkaline material, such as sodium hydroxide in 5~20 ml, preferably 10 ml water, and refluxing at 110 Celcius Degree at least two hours. Cooling the refluxed mixture to ambient temperature; obtaining the precipitate by a proper way, such as magnetic suction/pouring filtration; washing the precipitate in order by 2~20 ml, preferably 10 ml of water and acetone more than twice; then drying the washed precipitate. Aseptic filling the lipiodol solution (Guerbet, France) to the ferrofluid, by the ratio of ferrofluid to lipiodol, around 10% to 40% (g/ml), preferably 30% (g/ml), to form pre-lipiodol ferrofluid. Finally, dispersing or vibrating the pre-Lipiodol ferrofluid by ultrasound.

Lipiodol-ferrofluid including a $Fe_3O_4$ material according to a preferred embodiment of the present invention therefore is obtained. The particle size of the magnetic component, the $Fe_3O_4$ material ranges from 20 to 150 nm, preferably 60 to 100 nm.

Diethylenetriaminepentaacetic acid, mentioned above, could be replaced by an acid selected from the group consisting of 1,2-diamino-cyclohexyl tetraacetic acid, nitrile triacetic acid, ethylenediaminetetraacetic acid, salicylic acid, lactic acid, gluconic acid, maleic acid, undecenoic acid, oleic acid, tartaric acid, lauric acid, and caproic acid. The alkaline material, mentioned above, could be replaced by either ammonia or pyridine.

What is claimed is:

1. A lipiodol-ferrofluid, comprising:
   (a) ferrofluid, and
   (b) lipiodol; wherein the weight to volume ratio of said ferrofluid to said lipiodol ranges from 10 to 40% (g/ml).

2. The lipiodol-ferrofluid according to claim 1, wherein said ferrofluid includes a magnetic component having a particle size ranging from 20 to 150 nm.

3. The lipiodol-ferrofluid according to claim 2, wherein the magnetic component is selected from the group consisting of a $\gamma$-$Fe_2O_3$ material and a $Fe_3O_4$ material.

4. The lipiodol-ferrofluid according to claim 1, wherein said lipiodol is labeled an isotope selected from the group consisting of Y-90 and Re-188.

5. The lipiodol-ferrofluid according to claim 1, wherein the weight to volume ratio of said ferrofluid to said lipiodol is 30% (g/ml).

6. A process for preparing lipiodol-ferrofluid, comprising steps of:
   (a) preparing ferrofluid;
   (b) adding lipiodol to the ferrofluid by the weight to volume ratio of the ferrofluid to the lipiodol ranging from 10 to 40% (g/ml); and
   (c) dispersing the ferrofluid in the lipiodol.

7. The process according to claim 6, the ferrofluid prepared by said step (a) having a magnetic component having a particle size ranging from 20 to 150 nm.

8. The process according to claim 7, the magnetic component used in said step (a) being a $\gamma$-$Fe_2O_3$ material.

9. The process according to claim 8, the step (a) including sub-steps of:
   (a1) mixing 0.5~1.5 ml lipiodol, with 15~25 ml acetone, and a solution of 4~8 g ferrous chloride (containing 2~6hydrate) in 5~15 ml water to form a pre-mixture;
   (a2) adding 5~15 ml of an amine-containing solution and 30~50 ml acetone to the pre-mixture, and refluxing;
   (a3) subsequently dripping slowly a solution of 5~15 mg sodium nitrite in 10~30 ml water to the pre-mixture so as to form a mixture;
   (a4) continuing refluxing the mixture at 60 to 90 Celcius Degree; and
   (a5) drying a precipitate formed from the refluxed mixture.

10. The process according to claim 8, the step (a) including sub-steps of:
    (a1) mixing and stirring 1 ml lipiodol, with 20 ml acetone, and a solution of 6 g ferrous chloride (containing 4 hydrate) in 10 ml water to form a pre-mixture;
    (a2) adding 10 ml of an amine-containing solution and 40 ml acetone to the pre-mixture, and refluxing;
    (a3) subsequently dripping slowly a solution of 10 mg sodium nitrite in 20 ml water to the pre-mixture so as to form a mixture;
    (a4) continuing refluxing the mixture at 80 Celcius Degree; and
    (a5) drying a precipitate from the refluxed mixture.

11. The process according to claim 9, the amine-containing solution used in said step (a2) being selected from the group consisting of ethylenediamine solution, and hexamethylene-tetramine solution.

12. The process according to claim 9, the amine-containing solution of step (a2) being ethylenediamine solution.

13. The process according to claim 7, the magnetic component used in said step (a) being a $Fe_3O_4$ material.

14. The process according to claim 13, said step (a) including sub-steps of:
    (a1) mixing a solution of 5~9 g a metal complex complexing agent in 5~15 ml water, with a solution of 3~7 g ferrous sulphate (containing 5~9 hydrate) in 30~50 ml water to form a pre-mixture;
    (a2) refluxing the pre-mixture at 80 to 120 Celcius Degree;
    (a3) continuing refluxing and subsequently dripping slowly a solution of 1~5 g an alkaline material in 5~20 ml water to the pre-mixture so as to form a mixture; and
    (a4) drying a precipitate from the mixture.

15. The process according to claim 13, said step (a) including sub-steps of:
    (a1) mixing a solution of 7.8 g a metal complexing agent in 10 ml water, with a solution of 5.5 g ferrous sulphate (containing 7 hydrate) in 40 ml water to form a pre-mixture;
    (a2) refluxing the pre-mixture at 110 Celcius Degree;
    (a3) continuing refluxing and dripping slowly a solution of 3 g an alkaline material in 10 ml water to the pre-mixture so as to form a mixture; and
    (a4) drying a precipitate from the mixture.

16. The process according to claim 14, the metal complexing agent used in said step (a1) being selected from the group consisting of water-soluble salts of diethylenetriaminepentaacetic acid, 1,2-diamino-cyclohexyl tetraacetic acid, nitrile triacetic acid, ethylenediaminetetraacetic acid, salicylic acid, lactic acid, gluconic acid, maleic acid, undecenoic acid, oleic acid, tartaric acid, lauric acid, and caproic acid.

17. The process according to claim 14, the alkaline material used in said step (a3) being selected from the group consisting of sodium hydroxide, ammonia, and pyridine.

18. The process according to claim 6, further comprising labeling the lipiodol by an isotope selected from the group consisting of Y-90 and Re-188 prior to said step (b).

19. A pharmaceutical composition comprising the lipiodol-ferrofluid as defined in claim 1 and a pharmaceutical acceptable carrier; wherein lipiodol-ferrofluid can generate heat by high frequency waves, so as to eliminate of the target cells with a high temperature, having a range from 38 Celcius Degree to 50 Celcius Degree.

* * * * *